US012662564B2

(12) United States Patent
Shingai et al.

(10) Patent No.: US 12,662,564 B2
(45) Date of Patent: Jun. 23, 2026

(54) CURABLE COMPOSITION, STORAGE CONTAINER, AND THREE-DIMENSIONAL OBJECT PRODUCING METHOD

(71) Applicants: Yuki Shingai, Kanagawa (JP); Hiroyuki Naito, Tokyo (JP)

(72) Inventors: Yuki Shingai, Kanagawa (JP); Hiroyuki Naito, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 660 days.

(21) Appl. No.: 18/185,223

(22) Filed: Mar. 16, 2023

(65) Prior Publication Data

US 2023/0303747 A1 Sep. 28, 2023

(30) Foreign Application Priority Data

Mar. 22, 2022 (JP) ................................ 2022-046131

(51) Int. Cl.

| | |
|---|---|
| ***C08F 2/46*** | (2006.01) |
| ***A61K 6/16*** | (2020.01) |
| ***A61K 6/887*** | (2020.01) |
| ***B29C 64/129*** | (2017.01) |
| ***B33Y 10/00*** | (2015.01) |
| ***C08F 2/50*** | (2006.01) |
| ***C08F 220/14*** | (2006.01) |
| ***C08F 222/10*** | (2006.01) |
| ***C08G 61/04*** | (2006.01) |
| ***C08K 3/36*** | (2006.01) |
| ***C08K 9/06*** | (2006.01) |
| *B29K 35/00* | (2006.01) |
| *B33Y 70/00* | (2020.01) |
| *B33Y 80/00* | (2015.01) |

(52) U.S. Cl.

CPC .......... *C08F 222/1065* (2020.02); *A61K 6/16* (2020.01); *A61K 6/887* (2020.01); *B29C 64/129* (2017.08); *B33Y 10/00* (2014.12); *C08F 220/14* (2013.01); *C08F 222/102* (2020.02); *C08K 3/36* (2013.01); *C08K 9/06* (2013.01); *B29K 2035/00* (2013.01); *B29K 2995/0018* (2013.01); *B33Y 70/00* (2014.12); *B33Y 80/00* (2014.12); *C08K 2201/003* (2013.01); *C08K 2201/011* (2013.01)

(58) Field of Classification Search

CPC ...... C08K 9/06; C08K 3/36; C08K 2201/011; C08K 2201/003; A61K 6/887; A61K 6/16; B29C 64/129; B29C 64/112; B29K 2995/0018; B29K 2035/00; C08F 2/46; C08F 2/50; C08F 222/1065; C08F 222/102; C08F 220/14; C08G 61/04; B33Y 70/10; B33Y 70/00; B33Y 80/00; B33Y 10/00; C08L 33/10; C08L 33/08

USPC ........... 522/96, 90, 1, 6, 189, 184, 71; 520/1

See application file for complete search history.

(56) References Cited

U.S. PATENT DOCUMENTS

| | | | | |
|---|---|---|---|---|
| 2014/0239527 A1* | 8/2014 | Lee | B29C 64/106 264/17 |
| 2021/0137796 A1 | 5/2021 | Hosokawa et al. | |
| 2022/0306880 A1 | 9/2022 | Shingai et al. | |
| 2023/0045524 A1 | 2/2023 | Akizumi et al. | |

FOREIGN PATENT DOCUMENTS

| | | | |
|---|---|---|---|
| JP | 2013-071921 A | 4/2013 | |
| JP | 2021-035941 | 3/2021 | |
| JP | 2023-018917 | 2/2023 | |
| WO | 2021/131490 | 7/2021 | |
| WO | WO-2023007305 A1 * | 3/2023 | B29C 64/209 |

OTHER PUBLICATIONS

Fujita et al., "Effect of Base Monomer's Refractive Index on Curing Depth and Polymerization Conversion of Photo-cured Resin Composites", Dental Materials Journal, vol. 24, No. 3, Jul. 25, 2005, pp. 403-408.

Koubunshi Ronbunshu, "Highly Esthetic and Toughened Dental Composite Resins", The society of Polymer science, vol. 69, No. 3, Dec. 7, 2011, pp. 113-121, 10 pages with partial English translation.

Notice of Submission of Publications received for Japanese Patent Application No. JP2022-046131, mailed on May 13, 2025, 10 pages with English translation.

Extended European Search Report dated Jul. 20, 2023, in European Application No. 23162013.9, 7 pages.

* cited by examiner

*Primary Examiner* — Jessica Whiteley

(74) *Attorney, Agent, or Firm* — Grüneberg Global IP, PLLC

(57) ABSTRACT

A curable composition is provided. The curable composition contains a multifunctional urethane (meth)acrylate monomer (component 1), a (meth)acrylate monomer (component 2), and an inorganic filler (component 3). A mass content ratio (component 1:component 2) of the component 1 to the component 2 is from 65:35 through 40:60.

20 Claims, 2 Drawing Sheets

CURABLE COMPOSITION, STORAGE CONTAINER, AND THREE-DIMENSIONAL OBJECT PRODUCING METHOD

CROSS-REFERENCE TO RELATED APPLICATION

The present application claims priority under 35 U.S.C. § 119 to Japanese Patent Application No. 2022-046131, filed Mar. 22, 2022. The contents of which are incorporated herein by reference in their entirety.

BACKGROUND OF THE INVENTION

1. Field of the Invention

The disclosures herein generally relate to a curable composition, a storage container, and a three-dimensional object producing method.

2. Description of the Related Art

In recent years, among three-dimensional lamination manufacturing techniques, a material jetting method of deploying a curable composition at needed positions using an inkjet head, and curing the deployed curable composition by irradiation with active energy rays using, for example, a light irradiator, to produce a three-dimensional stereoscopic object has attracted attention (the method may hereinafter be referred to as MJ method).

In the MJ method, cured products of curable compositions need to have various properties such as strength, hardness, and elastic modulus. As a method for improving these properties, a method of adding an inorganic filler to the curable composition is being attempted.

Applications to biological materials represented by dental materials are also being studied, and there is a need of designing curable compositions by using biocompatible monomers. Curable compositions serving as bases and cured products thereof need to have not only mechanical properties, but also a high transparency in order that the cured products may have a desired color.

For example, a photopolymerizable dental composition for 3D printer use, proposed as a composition for producing a dental material, contains (a1) a (meth)acrylate monomer containing a urethane structure, (a2) a (meth)acrylate monomer free of a urethane structure, (b) an inorganic filler, and (c) a photopolymerization initiator, wherein the materials are contained at a predetermined mass ratio (for example, see Japanese Unexamined Patent Application Publication No. 2021-035941).

SUMMARY OF THE INVENTION

In one embodiment, a curable composition contains a multifunctional urethane (meth)acrylate monomer (component 1), a (meth)acrylate monomer (component 2), and an inorganic filler (component 3). A mass content ratio (component 1:component 2) of the component 1 to the component 2 is from 65:35 through 40:60.

DESCRIPTION OF THE PREFERRED EMBODIMENTS

Figure 1:
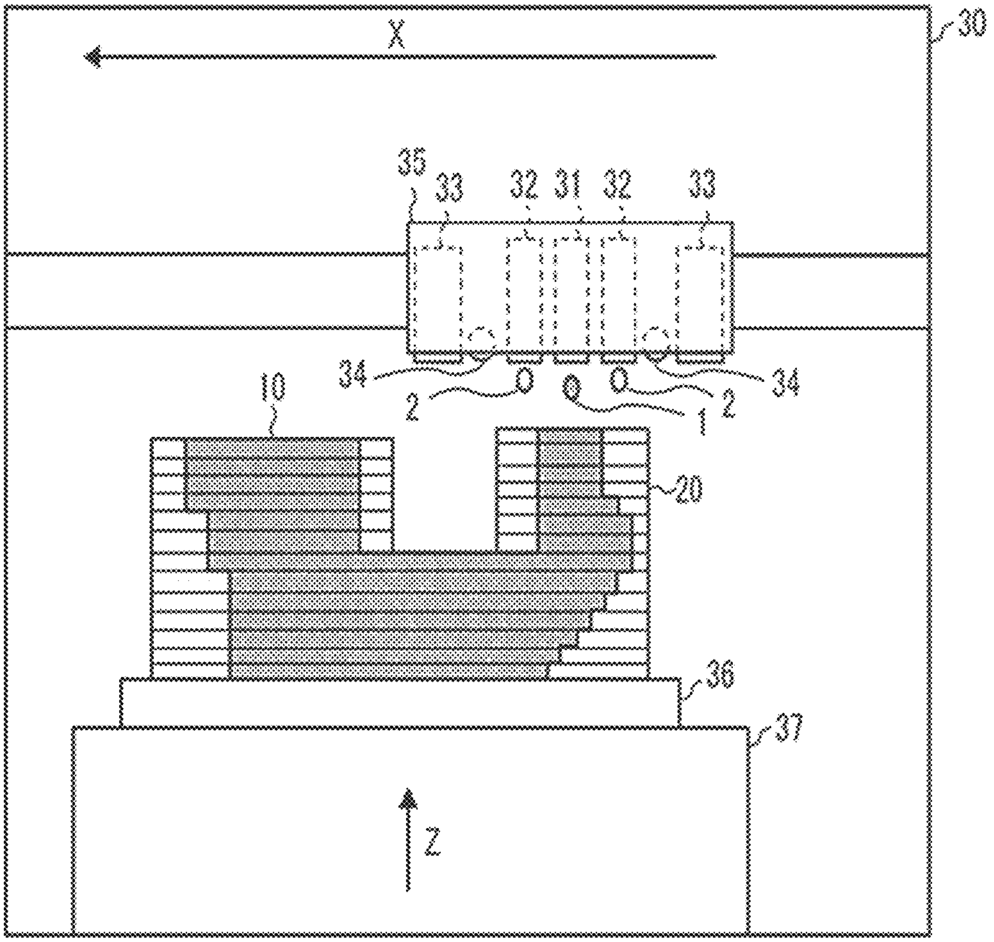
FIG. 1 is a schematic view illustrating an example of a three-dimensional object producing apparatus according to a three-dimensional object producing method of the present disclosure.

In the following, embodiments of the present invention will be described with reference to the accompanying drawings.

(Curable Composition)

A curable composition of the present disclosure contains a multifunctional urethane (meth)acrylate monomer (component 1), a (meth)acrylate monomer (component 2), and an inorganic filler (component 3). The curable composition of the present disclosure further contains other components as needed.

"Curable compositions" are compositions that cure by being irradiated with active energy rays or being heated, and form cured products. Examples of the curable compositions include active-energy-ray-curable compositions and thermosetting compositions.

Use of only inkjet types among the curable compositions is preferable. Inkjet active-energy-ray-curable compositions and inkjet thermosetting compositions are preferable, and inkjet active-energy-ray-curable compositions are more preferable.

In the present disclosure, "curing" means forming a polymer. However, "curing" is not limited to solidifying, but encompasses both thickening, and simultaneous occurrence of solidifying and thickening.

A "hardened product (cured product)" represents a polymer. However, a "hardened product (cured product)" is not limited to a solid, but encompasses a thickened product and a mixture of a solid and a thickened product.

In order to realize a high strength and a high transparency, existing techniques have proposed object production by stereolithography using active-energy-ray-curable compositions containing urethane di(meth)acrylate. However, there is a problem that the mentioned monomer has an extremely high viscosity and cannot be used in an inkjet method.

It has also been known to add inorganic fillers to compositions in order to improve mechanical properties. However, there is a problem that inorganic fillers increase the viscosity of the compositions and make the compositions difficult to discharge by an inkjet method. Furthermore, objects produced with compositions containing inorganic fillers are problematic in terms of transparency.

The present inventors have found that a high-viscosity multifunctional urethane (meth)acrylate (component 1) from which a cured product having a high transparency and a high strength can be obtained can become inkjet (IJ)-dischargeable when a (meth)acrylate monomer (component 2) serving as a low-viscosity monomer component is added to the high-viscosity multifunctional urethane (meth)acrylate (component 1) at a predetermined mass ratio, and have found it possible to obtain a cured product having a high transparency and a high strength.

Moreover, the present inventors have found it possible to obtain a composition from which a cured product (three-dimensional object) having a high mechanical property (high strength) and a high transparency (i.e., little structural opalescence or iridescence) can be obtained, by adding a transparent inorganic filler (silica) to the composition.

The present disclosure has an object to provide a curable composition that has a good inkjet dischargeability and can produce a cured product having a high strength and a high transparency at the same time.

The present disclosure can provide a curable composition that has a good inkjet dischargeability and can produce a cured product having a high strength and a high transparency at the same time.

In the present disclosure, something is defined as "having transparency" when the total light transmittance through the something measured according to Japanese Industrial Standards (JIS) K 7361-1/HAZE: JIS K 7136 is 60% or higher.

The total light transmittance can be measured by the following method.

Figure 2:
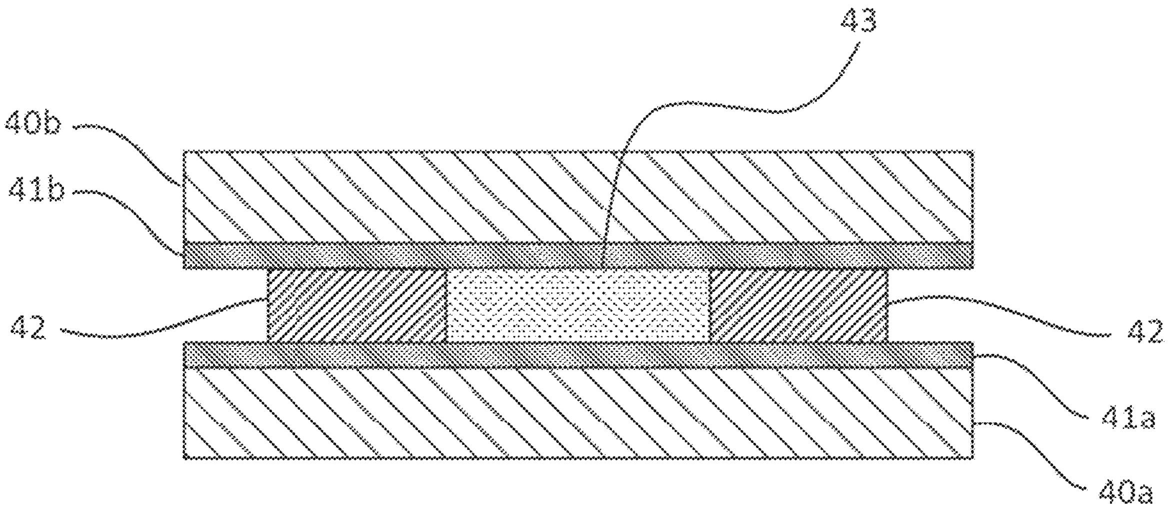
FIG. 2 is a view illustrating an example of a method for producing a sample for measuring total light transmittance in Examples.

As illustrated in FIG. 2, an OHP sheet 41*a* is placed on a glass substrate 40*a*, and a silicon mold 42 (shape: a length of 20 mm on each side, and a thickness of 1 mm) is tightly attached on the OHP sheet 41*a*. Next, the silicon mold 42 is filled with a curable composition 43, which is the target of measurement, and covered with an OHP sheet 41*b*, which is further covered with a glass substrate 40*b*. Next, using an ultraviolet irradiator (device name: SPOT CURE SP5-250DB, available from Ushio Inc.), the curable composition is irradiated with ultraviolet rays having an irradiation intensity of 200 $mW/cm^2$ for 10 minutes through the glass substrate 40*b*. Next, using the ultraviolet irradiator, the curable composition is irradiated with ultraviolet rays having an irradiation intensity of 200 $mW/cm^2$ for 10 minutes through the glass substrate 40*a* at the side that is opposite to the side irradiated with ultraviolet rays first. Next, the OHP sheet 41*b* is peeled, and a cured product, which is the curable composition having been cured, is taken out from the silicon mold 42 and left in a stationary state in an environment at a temperature of 23° C. at a relative humidity of 50% for 24 hours, to obtain a test piece having a thickness of 1 mm.

The total light transmittance (Tt) through the test piece produced above is measured using a DIRECT READING HAZEMETER (available from Toyo Seiki Seisaku-sho, Ltd.) according to JIS K 7361-1/HAZE: JIS K 7136.

Examples of the method for measuring the total light transmittance through a three-dimensional object produced using the curable composition include a method of measuring the total light transmittance through a processed product obtained by processing the three-dimensional object to a thickness of 1 mm using a metal file or by cutting, polishing both sides of the three-dimensional object with waterproof abrasive paper P600 or with anything of the same level, and glossily polishing both sides of the three-dimensional object with alumina abrasive powder suspended in water and with felt.

Whatever size the processed product or the portion cut out from the three-dimensional object has or whatever measuring instrument is used, it is possible to measure the total light transmittance through the processed product, so long as the measurement includes the step of polishing both sides of the processed product with waterproof abrasive paper P600 or with anything of the same level, and glossily polishing both sides of the processed product with alumina abrasive powder suspended in water and with felt.

The curable composition of the present disclosure contains monomer components including a multifunctional urethane (meth)acrylate monomer (component 1) and a low-viscosity (meth)acrylate monomer (component 2), and an inorganic filler (component 3), preferably contains a polymerization initiator, and further contains other components as needed.

<Monomer Components>

The monomer components include a multifunctional urethane (meth)acrylate monomer (component 1) and a low-viscosity (meth)acrylate monomer (component 2), and further include other monomers as needed.

<<Multifunctional Urethane (Meth)Acrylate Monomer (Component 1)>>

Examples of the multifunctional urethane (meth)acrylate monomer (component 1) include aliphatic urethane (meth) acrylate monomers and aromatic urethane (meth)acrylate monomers.

The number of functional groups in the component 1 is not particularly limited, may be appropriately selected in accordance with the intended purpose, and may be, for example, two and three.

Examples of the component 1 include 1,6-bis(methacryloyloxy-2-ethoxycarbonylamino)-2,4,4-trimethylhexane (urethane dimethacrylate) represented by Structural formula (1) below.

Structural formula (1)

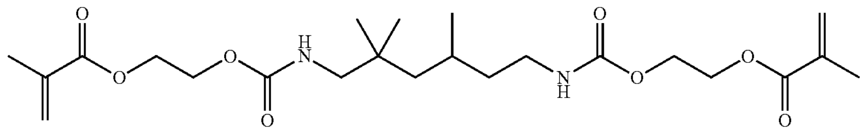

As the component 1, a synthesized product or a commercially available product may be used.

Examples of the commercially available product include diurethane methacrylate, and mixed isomers (e.g., compound name: 1,6-bis(methacryloyloxy-2-ethoxycarbonylamino)-2,4,4-trimethylhexane, available from Sigma-Aldrich Co. LLC).

It is preferable that the refractive index $n25D_{(1)}$ of the multifunctional urethane (meth)acrylate monomer (component 1) be close to the refractive index $n25D_{(3)}$ of the inorganic filler (component 3) specified below. When the refractive index $n25D_{(1)}$ is close to the refractive index $n25D_{(3)}$, it is possible to improve transparency of a cured product of the curable composition.

The refractive index $n25D_{(1)}$ of the component 1 is measured by the following method.

[Method for Measuring the Refractive Index $n25D_{(1)}$ of the Component 1]

The refractive index represents refractive index nD measured under D-rays (light having a wavelength of 589.3 nm) of a sodium-vapor lamp by a B method using an Abbe's refractometer and stipulated by JIS K 7142. For example, it is possible to measure the refractive index of the component 1 using an Abbe's refractometer NAR-1T (available from Atago Co., Ltd.) under D-rays (589.3 nm) of a light source lamp at 25° C.

To know the refractive index of the component 1 before being cured, the component 1 may be identified by such a method as mass spectrometry, and the safety data sheet or the catalog of a commercially available product of the identified component 1 may be consulted for the value concerned.

It is possible to identify the refractive index $n25D_{(1)}$ of the component 1 from a cured product of the composition. Specifically, it is possible to identify the monomer contained in the composition by, for example, pyrolytic Gas Chromatography-Mass Spectrometry (GC-MS), Fourier-Transform InfraRed spectroscopy (FT-IR), micro-Raman spectroscopy, various methods of Nuclear Magnetic Resonance (NMR), and Time-Of-Flight Secondary Ion Mass Spectrometry (TOF-SIMS). Then, it is possible to identify and calculate the refractive index $n25D_{(1)}$ of the component 1 in accordance with the compositional ratio in the composition in view of a publicly-known refractive index of a commercially available product when the identified monomer is a commercially available product, or in view of a refractive index of the identified monomer measured using an Abbe's refractometer at 25° C.

The refractive index $n25D_{(1)}$ of the component 1 and the refractive index $n25D_{(3)}$ of the component 3 are defined as being close when the refractive index difference $\Delta n25D_{(1\_3)}$ between the refractive index $n25D_{(1)}$ of the component 1 and the refractive index $n25D_{(3)}$ of the component 3 is less than on or equal to a certain value.

In the present specification, a refractive index difference represents the absolute value of the calculated value.

The refractive index difference $\Delta n25D_{(1\_3)}$ between the refractive index $n25D_{(1)}$ of the component 1 and the refractive index $n25D_{(3)}$ of the component 3 is preferably 0.07 or less, and more preferably 0.04 or less. When the refractive index difference $\Delta n25D_{(1\_3)}$ is 0.07 or less, it is possible to improve transparency of a cured product of the curable composition.

The method for measuring the refractive index $n25D_{(3)}$ of the component 3 will be described below.

The refractive index $n25D_{(1)}$ of the component 1 is preferably 1.50 or lower, and more preferably 1.43 or higher and 1.49 or lower. When the refractive index $n25D_{(1)}$ of the component 1 is 1.50 or lower, it is possible to improve transparency of a cured product (three-dimensional object).

The viscosity of the component 1 at 25° C. is not particularly limited, may be appropriately selected in accordance with the intended purpose, and may be, for example, 8,000 mPa·s or higher and 30,000 mPa·s or lower.

The viscosity at 25° C. can be measured by a routine method. For example, the viscosity can be measured by a cone plate rotary viscometer (VISCOMETER TVE-22L, manufactured by TOKI SANGYO CO., LTD.) using a cone rotor (1° 34'×R24) at a number of rotation of 50 rpm at a hematothermal circulating water temperature of 25° C.

The content of the component 1 is preferably 40% by mass or greater and 65% by mass or less and more preferably 50% by mass or greater and 60% by mass or less relative to the whole amount of the curable composition.

The mass ratio (component 1:component 2) between the content of the component 1 and the content of the component 2 is from 65:35 through 40:60. The details will be described below.

<<(Meth)Acrylate Monomer (Component 2)>>

Examples of the (meth)acrylate monomer (component 2) include (meth)acrylate monomers having a viscosity of 100 mPa·s or lower at 25° C.

A composition containing the component 2 can have a reduced viscosity of the component 1 and can produce a cured product having a high strength.

The method for measuring the viscosity of the component 2 at 25° C. is the same as the method for measuring the viscosity of the component 1 before being cured.

The component 2 is not particularly limited and may be appropriately selected in accordance with the intended purpose so long as the component 2 is a (meth)acrylate monomer. Examples of the component 2 include mono(meth)acrylates, di(meth)acrylates, and trifunctional or greater (meth)acrylates. Among these (meth)acrylate monomers, di(meth)acrylates are preferable in terms of easy availability and mechanical properties of a cured product.

Examples of the component 2 include difunctional di(meth)acrylates represented by General formula (2) below, such as ethylene glycol dimethacrylate (n=1) and diethylene glycol dimethacrylate (n=2).

General formula (2)

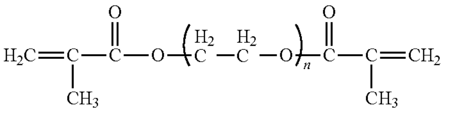

It is preferable that a monofunctional (meth)acrylate be contained as the component 2.

The refractive index n25D of the monofunctional meth (acrylate) before being cured is preferably 1.48 or lower and more preferably 1.42 or higher and 1.47 or lower.

Examples of the monofunctional (meth)acrylate include methyl methacrylate, hydroxyethyl methacrylate, ethyl methacrylate, and butyl methacrylate.

The refractive index $n25D_{(2)}$ of the component 2 is preferably 1.48 or lower and more preferably 1.42 or higher and 1.47 or lower.

The refractive index $n25D_{(2)}$ of the component 2 can be measured by the same method as the method for measuring the component 1.

The refractive index difference $\Delta n25D_{(2\_3)}$ between the refractive index $n25D_{(2)}$ of the component 2 and the refractive index $n25D_{(3)}$ of the component 3 is preferably 0.07 or less and more preferably 0.04 or less. When the refractive index difference $\Delta n25D_{(2\_3)}$ is 0.07 or less, it is possible to improve transparency of a cured product of the curable composition.

The viscosity of the component 2 at 25° C. is not particularly limited, may be appropriately selected in accordance with the intended purpose, and is preferably, for example, 100 mPa·s or lower and more preferably 50 mPa·s or lower.

The content of the component 2 is preferably 35% by mass or greater and 60% by mass or less and more preferably 40% by mass or greater and 50% by mass or less relative to the whole amount of the curable composition.

In the monomer components, the mass content ratio (component 1:component 2) of the component 1 to the component 2 is from 65:35 through 40:60, preferably 55:45, and more preferably 60:40. When the mass content ratio (component 1:component 2) of the component 1 to the component 2 is from 65:35 through 40:60, it is possible to obtain a curable composition that can produce a cured product having a high strength and a high transparency, and has a viscosity at which the curable composition is inkjet-dischargeable.

In general, a termination reaction in radical polymerization occurs between two growing radical molecules. As the monomer components increasingly polymerize and grow a polymer, the viscosity of the polymerizing system increases and the chain-termination reaction speed decreases significantly Moreover, as the degree of polymerization of the polymer increases, the polymerization speed increases significantly.

The present disclosure finds it possible to do without excessively reducing the mass ratio of the component 1 in order that a curable composition can be discharged by an inkjet method and can produce a cured product in which the properties of a cured product of the component 1 (i.e., a high transparency and a high strength) are maintained, provided that the mass content ratio (component 1:component 2) between the content of the component 1 and the content of the component 2 in the curable composition is from 65:35 through 40:60.

The present inventors have found it possible to inhibit progress of termination reaction in radical polymerization and to maintain transparency of a cured product (three-dimensional object), by compositionally adjusting the curable composition in a manner that the viscosity of the polymerizing system will not decrease excessively until a middle term of the radical polymerization.

<Inorganic Filler (Component 3)>

The inorganic filler (component 3) is not particularly limited and may be appropriately selected in accordance with the intended purpose. Examples of the inorganic filler include alumina, talc, silica, titania, zirconia, magnesium silicate, mica, glass fiber, glass bead, carbon black, carbon fiber, and aluminum ball. One of these inorganic fillers may be used alone or two or more of these inorganic fillers may be used in combination. Among these inorganic fillers, silica, alumina, titania, and zirconia are preferable.

It is preferable that the component 3 has a particulate shape.

Examples of the shapes of the component 3 having the particulate shape include a spherical shape and an irregular shape. Of these shapes, a spherical shape is preferable in terms of dispersibility and inkjet dischargeability.

The "spherical shape" is not limited to a true spherical shape, but encompasses, for example, a spheroid and a polyhedron. For example, the "spherical shape" according to the present disclosure includes, but is not limited to, a particle in which a diameter (longer diameter) that extends over the longest length to the contour by passing the center of the particle is approximately twice as long as a diameter (shorter diameter) that extends over the shortest length to the contour by passing the center of the particle. The ratio of the shorter diameter to the longer diameter is preferably from 1:1 through 1:5, and more preferably from 1:1 through 1:2.

The structure of the component 3 is not particularly limited and may be appropriately selected in accordance with the intended purpose.

It is preferable that the particles of the component 3 contain carbon in the surface.

Carbon is not particularly limited. Examples of carbon include a compound containing carbon.

Examples of the compound containing carbon include a surface reforming agent.

Examples of the surface reforming agent include a silane coupling agent.

When the particles of the component 3 contain carbon in the surface, it is possible to improve dispersion stability of the component 3 serving as the inorganic filler in an ink.

The content of carbon is preferably 0.5% by mass or greater and 1.5% by mass or less and more preferably 0.7% by mass or greater and 1.2% by mass or less relative to the mass of the particles of the inorganic filler. When the content of carbon is 0.5% by mass or greater and 1.5% by mass or less relative to the whole amount of the silica particles, it is possible to improve dispersion stability of the inorganic filler in an ink and to increase interfacial adhesion between the resin and the inorganic filler in a cured product.

It is possible to measure the content of carbon by heating the inorganic filler to 600° C. through temperature elevation at 10° C./min and determining a reduction in the weight according to the Thermo Gravimetry-Differential Thermal Analysis (TG-DTA).

The silane coupling agent is not particularly limited and may be appropriately selected in accordance with the intended purpose. Examples of the silane coupling agent include vinyl methoxysilane, vinyl ethoxysilane, 2-(3,4-epoxycyclohexyl)ethyl trimethoxysilane, 3-glycidoxypropyl methyl dimethoxysilane, 3-glycidoxypropyl trimethoxysilane, 3-glycidoxypropyl methyl diethoxysilane, 3-glycidoxypropyl triethoxysilane, styryl p-styryl trimethoxysilane, 3-methacryloxypropyl methyl dimethoxysilane, 3-methacryloxypropyl trimethoxysilane, 3-methacryloxypropyl methyl diethoxysilane, 3-methacyrloxypropyl triethoxysilane, 3-acryloxypropyl trimethoxysilane, N-2-(aminoethyl)-3-aminopropyl methyl dimethoxysilane, N-2-(aminoethyl)-3-aminopropyl methyl dimethoxysilane, 3-aminopropyl trimethoxysilane, 3-aminopropyl triethoxysilane, 3-triethoxysilyl-N-(1,3-dimethyl-butylidene)propylamine, N-phenyl-3-aminopropyl trimethoxysilane, hydrochloride of N-(vinylbenzyl)-2-aminoethyl-3-aminopropyl trimethoxysilane, tris-(trimethoxysilylpropyl)isocyanurate, 3-ureidopropyl trialkoxysilane, 3-mercaptopropyl methyl dimethoxysilane, 3-mercaptopropyl trimethoxysilane, 3-isocyanrate propyl triethoxysilane, and 3-trimethoxysilylpropyl succinic anhydride. One of these silane coupling agents may be used alone or two or more of these silane coupling agents may be used in combination.

Among these silane coupling agents, silane coupling agents containing an unsaturated double bond, such as vinyl methoxysilane, 3-methacryloxypropyl methyl dimethoxysilane, and 3-acryloxypropyl trimethoxysilane, are particularly preferable.

The volume mean primary particle diameter of the component 3 is preferably 10 nm or greater and 300 nm or less and more preferably 50 nm or greater and 250 nm or less. When the volume mean primary particle diameter of the component 3 is 10 nm or greater and 300 nm or less, transparency of the curable composition can be improved.

The volume mean primary particle diameter can be measured by, for example, a dynamic light scattering method. The volume mean primary particle diameter of a product obtained by diluting a dispersion liquid of the inorganic filler in the monomers contained in the composition 100-fold with 2-methoxy-1-methyl ethyl acetate or with the monomers may be measured using a measuring instrument ELS-Z available from Otsuka Electronics Co., Ltd.

The refractive index $n20D_{(3)}$ of the component 3 is preferably 1.40 or higher and 1.50 or lower and more preferably 1.43 or higher and 1.47 or lower. When the refractive index $n20D_{(3)}$ of the component 3 is 1.40 or higher and 1.50 or lower, the component 3 can have small refractive index differences from the component 1 and the component 2. Hence, it is possible to improve transparency of a cured product of the curable composition while also improving strength of the cured product.

The refractive index $n25D_{(3)}$ of the component 3 can be measured by the same method as the method for measuring the component 1.

The content of the component 3 is preferably 20% by mass or greater and 60% by mass or less and more preferably 25% by mass or greater and 40% by mass or less relative to the total amount of the component 1 and the component 2. When the content of the component 3 is 20% by mass or greater and 60% by mass or less relative to the total amount of the component 1 and the component 2, it is possible to improve strength of a cured product of the curable composition.

<Polymerization Initiator>

As the polymerization initiator, a desirably selected substance that generates radicals in response to irradiation with light (particularly, ultraviolet rays having a wavelength of from 220 nm through 400 nm) can be used.

Examples of the polymerization initiator include acetophenone, 2,2-diethoxyacetophenone, p-dimethylaminoacetophenone, benzophenone, 2-chlorobenzophenone, p,p'-chlorobenzophenone, p,p-bisdiethylaminobenzophenone, Michler's ketone, benzyl, benzoin, benzoin methyl ether, benzoin ethyl ether, benzoin isopropyl ether, benzoin-n-propyl ether, benzoin isobutyl ether, benzoin-n-butyl ether, benzyl dimethyl ketal, thioxanthone, 2-chlorothioxanthone, 2-hydroxy-2-methyl-1-phenyl-1-one, 1-(4-isopropylphenyl) 2-hydroxy-2-methylpropan-1-one, methyl benzoyl formate, 1-hydroxycyclohexyl phenyl ketone, azobis isobutyronitrile, benzoyl peroxide, and di-tert-butyl peroxide. One of these polymerization initiators may be used alone or two or more of these polymerization initiators may be used in combination.

The content of the polymerization initiator is preferably 0.1% by mass or greater and 10.0% by mass or less and more preferably 1.0% by mass or greater and 5.0% by mass or less relative to the whole amount of the curable composition.

<Other Components>

The other components are not particularly limited and may be appropriately selected in accordance with the intended purpose. Examples of the other components include a surfactant, a polymerization inhibitor, a coloring material, a viscosity modifier, an antioxidant, a crosslinking accelerator, an ultraviolet absorbent, a plasticizer, a preservative, a solvent, and a dispersant.

<<Surfactant>>

As the surfactant, for example, a compound having a molecular weight of 200 or greater and 5,000 or less is preferable. Specific examples of such a surfactant include PEG-type nonionic surfactants [e.g., an adduct of nonylphenol with from 1 mole through 40 moles of ethylene oxide (hereinafter, abbreviated as EO), and an adduct of stearic acid with from 1 mole through 40 moles of EO], multivalent alcohol-type nonionic surfactants (e.g., sorbitan palmitic acid monoester, sorbitan stearic acid monoester, and sorbitan stearic acid triester), fluorine-containing surfactants (e.g., an adduct of perfluoroalkyl with from 1 mole through 50 moles of EO, perfluoroalkyl carboxylate, and perfluoroalkyl betaine), and modified silicone oils [e.g., polyether-modified silicone oil and (meth)acrylate-modified silicone oil]. One of these surfactants may be used alone or two or more of these surfactants may be used in combination.

<<Polymerization Inhibitor>>

Examples of the polymerization inhibitor include phenol compounds [e.g., hydroquinone, hydroquinone monomethyl ether, 2,6-di-t-buytl-p-cresol, 2,2-methylene-bis-(4-methyl-6-t-butylphenol), and 1,1,3-tris-(2-methyl-4-hydroxy-5-t-butylphenyl)butane], sulfur compounds [e.g., dilauryl thio dipropionate], phosphorus compounds [e.g., triphenyl phosphite], and amine compounds [e.g., phenothiazine]. One of these polymerization inhibitors may be used alone or two or more of these polymerization inhibitors may be used in combination.

<<Coloring Material>>

As the coloring material, dyes or pigments that can dissolve or stably disperse in the curable composition and have an excellent thermal stability are suitable. Among such dyes or pigments, solvent dyes are preferable. Two or more coloring materials may be appropriately mixed for, for example, color adjustment.

<<Dispersant>>

The dispersant is an additive that has a function of adsorbing to the surface of a solid component to make the solid component stably disperse in the curable composition. As the dispersant, a publicly-known dispersant can be appropriately used.

<<Organic Solvent>>

The curable composition optionally contains an organic solvent although it is preferable to not include it. The curable composition free of an organic solvent, in particular, volatile organic compound (VOC), is preferable because it enhances safety at where the composition is handled and makes it possible to prevent pollution of the environment. Incidentally, the "organic solvent" represents a common non-reactive organic solvent, for example, ether, ketone, xylene, ethyl acetate, cyclohexanone, and toluene, which is clearly distinguished from polymerizable compounds. Furthermore, "free of" an organic solvent means that no organic solvent is substantially contained (for example, to an extent at which the properties of the organic solvent affect the composition). The content thereof is preferably less than 0.1% by mass.

<<Water>>

The curable composition optionally contains water although it is preferable that the curable composition be free of water, if possible. "Free of" water means that substantially no water is contained (for example, to an extent at which the properties of the water affect the composition). The content thereof is preferably less than 1.0% by mass. When the content of the water is less than or equal to a certain amount, it is possible to inhibit, for example, reduction in curing speed, reduction in curing strength, increase in water absorbency, and reduction in separability from a support part forming material described below.

[Method for Preparing Curable Composition]

It is possible to prepare the curable composition of the present disclosure by using the various components described above. The method and conditions for preparing the curable composition are not particularly limited. For example, it is possible to prepare the curable composition by subjecting the component 1, the component 2, the component 3, and the other components to dispersion treatment using a disperser such as a ball mill, a kitty mill, a disk mill, a pin mill, and a DYNO-MILL.

[Properties of Curable Composition]

It is preferable that the curable composition of the present disclosure has a low viscosity in terms of, for example, dischargeability through a nozzle. Hence, according to an aspect, the viscosity of the curable composition of the present disclosure is preferably 400 mPa·s or lower, more preferably 300 mPa·s or lower, and yet more preferably 200 mPa·s or lower at 25° C. Moreover, the viscosity of the curable composition is preferably 10 mPa·s or higher at 25° C. in terms of dischargeability and object production accuracy. During object production, by adjusting the temperature of an inkjet head or of a flow path, it is possible to adjust the viscosity of the curable composition.

For example, the viscosity can be measured by a cone plate rotary viscometer (VISCOMETER TVE-22L, manufactured by TOKI SANGYO CO., LTD.) using a cone rotor (1° 34'×R24) at a number of rotation of 50 rpm at a hematothermal circulating water temperature of 25° C.

It is preferable that a curable composition that can be used in an inkjet use has a static surface tension of 20 mN/m or higher and 40 mN/m or lower at 25° C. in terms of discharging stability and object production accuracy.

The static surface tension can be measured by a routine method. Examples of the routine method include a plate method, a ring method, and a pendant drop method.

The curable composition of the present disclosure can be cured by, for example, irradiation with active energy rays.

The active energy rays are not particularly limited and may be appropriately selected in accordance with the intended purpose. Examples of the active energy rays include active energy rays that are able to give necessary energy for allowing polymerization reaction of polymerizable components in the composition to proceed, such as electron beams, α-rays, β-rays, γ-rays, and X-rays, in addition to ultraviolet rays. When a light source having a particularly high energy among these kinds of active energy rays is used, polymerization reaction can be allowed to proceed without a polymerization initiator.

When ultraviolet rays are used as the active energy rays for irradiation, mercury-free is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long working life, high efficiency, and high cost performance make such irradiation sources desirable.

The curable composition of the present disclosure can be suitably used for inkjet uses, particularly, for production of three-dimensional objects by inkjet. Hence, the present disclosure also includes a three-dimensional object produced using the curable composition of the present disclosure.

(Storage Container)

A storage container of the present disclosure stores the curable composition of the present disclosure. That is, the storage container of the present disclosure represents a container in a state of storing the curable composition.

The storage container that stores the curable composition of the present disclosure can be used as a cartridge or a bottle. Therefore, users can avoid direct contact with the curable composition during operations such as conveyance or replacement of the curable composition, so that fingers and clothes are prevented from contamination.

Furthermore, inclusion of foreign matters such as dust in the curable composition can be inhibited.

In addition, the container can be of any size, any form, and any material. For example, the container can be designed to a particular application. It is preferable to use a light blocking material to block the light or cover the container with a light blocking sheet, etc.

(Three-Dimensional Object Producing Method and Three-Dimensional Object Producing Apparatus)

A three-dimensional object producing method of the present disclosure includes a discharging step of discharging the curable composition of the present disclosure by an inkjet method, and a curing step of curing the curable composition by irradiation with active energy rays, and further includes other steps as needed.

A three-dimensional object producing apparatus of the present disclosure includes a storage container storing the curable composition of the present disclosure, a discharging unit configured to discharge the curable composition of the present disclosure by an inkjet method, and a curing unit configured to cure the curable composition by irradiation with active energy rays, and further includes other units as needed.

<Discharging Step and Discharging Unit>

The discharging step is a step of discharging the curable composition of the present disclosure by an inkjet method, and is performed by the discharging unit.

The discharging unit is a unit configured to discharge the curable composition of the present disclosure by an inkjet method. The type of the discharging method is not particularly limited, and examples of the type include a continuous jetting type, and an on-demand type. Examples of the on-demand type include a piezo type, a thermal type, and an electrostatic type.

In the discharging step, it is preferable to discharge the curable composition of the present disclosure by an inkjet method onto a stage having an ascending/descending function. The curable composition discharged onto the stage forms a liquid film.

<Curing Step and Curing Unit>

The curing step is a step of curing the curable composition by irradiation with active energy rays.

The curing unit is a unit configured to cure the curable composition by irradiation with active energy rays.

The curing step is suitably performed by the curing unit.

In the curing step, the liquid film of the curable composition formed on the stage is cured by irradiation with active energy rays.

—Active Energy Rays—

Active energy rays that can be suitably used for curing the curable composition are light, and, in particular, ultraviolet rays having a wavelength of from 220 nm through 400 nm. The active energy rays are not particularly limited, so long as they are able to give necessary energy for allowing polymerization reaction of polymerizable components in the composition to proceed. Examples of the active energy rays include electron beams, α-rays, β-rays, γ-rays, and X-rays, in addition to ultraviolet rays. When a light source having a particularly high energy is used, polymerization reaction can be allowed to proceed without a polymerization initiator. In the case of irradiation with ultraviolet rays, mercury-free is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long working life, high efficiency, and high cost performance make such irradiation sources desirable.

<Other Steps and Other Units>

Examples of the other steps include a smoothing step.

Examples of the other units include a smoothing unit.

<<Smoothing Step and Smoothing Unit>>

The smoothing step is a step of smoothing the surface of the liquid film formed of the curable composition discharged in the discharging step.

In the smoothing step, any excessive portion of the curable composition discharged is scraped away, to smooth out roughness of the liquid film or the layer formed of the curable composition.

The smoothing step is suitably performed by the smoothing unit

The smoothing unit is not particularly limited and may be appropriately selected in accordance with the intended purpose. Examples of the smoothing unit include a roller.

The three-dimensional object producing method of the present disclosure produces a three-dimensional object having a desired shape by repeating the discharging step and the curing step in order.

The three-dimensional object producing method and the three-dimensional object producing apparatus will be described below by taking, for example, a case where the curable composition of the present disclosure is used as a model part forming material.

FIG. 1 is a schematic view illustrating an example of the three-dimensional object producing apparatus of the present disclosure. A three-dimensional object producing apparatus 30 of FIG. 1 includes head units 31 and 32, ultraviolet irradiators 33, rollers 34, a carriage 35, and a stage 37. The head unit 31 is configured to discharge a model part forming material 1. The head units 32 are configured to discharge a support part forming material 2. The rollers 34 are configured to smooth a liquid film of the model part forming material 1 and the support part forming material 2. The ultraviolet irradiators 33 are configured to cure the discharged model part forming material 1 and the discharged support part forming material 2 by irradiation with ultraviolet rays. The carriage 35 is configured to move the respective units such as the head units 31 and 32 in the X direction of FIG. 1 in a go-and-return manner. The stage 37 is configured to move a substrate 36 in the Z direction indicated in FIG. 1 and in the Y direction, which is a direction perpendicular to the sheet of FIG. 1. Instead of the stage 37, the carriage 35 may be configured to move in the Y direction.

When there are a plurality of model part forming materials color by color, the three-dimensional object producing apparatus 30 may include a plurality of head units 31 configured to discharge the model part forming materials of the respective colors. As the nozzles of the head units 31 and 32, nozzles of a publicly-known inkjet printer can be suitably used.

Examples of metals that can be used as the rollers 34 include SUS 303 series, SUS 400 series, and SUS 60 series, hexavalent chromium, silicon nitride, and tungsten carbide. Any of these metals may be coated with, for example, fluorine or silicone and used as the rollers 34. Among these metals, SUS 600 series are preferable in terms of strength and processability.

When applying the rollers 34, the three-dimensional object producing apparatus 30 laminates layers while moving down the stage 37 in accordance with the number of times layers are laminated in order to keep a constant gap between the rollers 34 and the surface of the object. In a preferred configuration, the rollers 34 are disposed near the ultraviolet irradiators 33.

The three-dimensional object producing apparatus 30 may be equipped with caps or the like for closing the nozzles of the head units 31 and 32, as measures against drying of an ink (corresponding to the curable composition of the present disclosure) during a halt of the operation. Moreover, the three-dimensional object producing apparatus 30 may include a maintenance mechanism configured to maintain the heads in order to inhibit clogging of the nozzles that are used continuously for a long period of time.

An object (cured product) producing step that is performed by the three-dimensional object producing apparatus of the present disclosure and in which the discharging step and the curing step are repeated in order will be described below.

While moving the carriage 35 or the stage 37, the engine of the three-dimensional object producing apparatus 30 causes the head unit 31 to discharge liquid droplets of the model part forming material 1 and the head units 32 to discharge liquid droplets of the support part forming material 2 based on two-dimensional data representing the bottommost cross-section among input two-dimensional data. As a result, the liquid droplets of the model part forming material 1 are deployed at the positions corresponding to the pixels indicating the model part in the two-dimensional data representing the bottommost cross-section, the liquid droplets of the support part forming material 2 are deployed at the positions corresponding to the pixels indicating the support part in the same two-dimensional data, and a liquid film in which the liquid droplets of adjoining positions contact each other is formed. When the number of objects to be formed is one, a liquid film having a cross-sectional shape is formed in the center of the stage 37. When the number of objects to be formed is a plural number, the three-dimensional object producing apparatus 30 may form a plurality of liquid films having respective cross-sectional shapes on the stage 37, or may stack a liquid film on an object produced previously.

It is preferable to install heaters in the head units 31 and 32. It is also preferable to install pre-heaters on a path through which the model part forming material is supplied to the head unit 31 and on a path through which the support part forming material is supplied to the head units 32.

In the smoothing step, the rollers 34 smooth out roughness of the liquid film or the layer formed of the model part forming material and the support part forming material by scraping away any excessive portions of the model part forming material and the support part forming material that are discharged onto the stage 37. The smoothing step may be performed once every time a layer is laminated in the Z-axis direction, or may be performed once every time from two through fifty layers are laminated. In the smoothing step, the rollers 34 may be stopped or may rotate at a positive or negative relative speed with respect to the travelling direction of the stage 37. The rotation speed of the rollers 34 may be a constant speed, a constant acceleration, or a constant deceleration. The number of rotations of the rollers 34 expressed as the absolute value of the relative speed with respect to the stage 37 is preferably 50 mm/s or greater and 400 mm/s or less. When the relative speed is extremely low, smoothing is insufficient and smoothness is adversely affected. When the relative speed is extremely high, a large-sized apparatus is needed, liquid droplets discharged may fall out of place due to, for example, vibration, and smoothness may be reduced as a result. In the smoothing step, it is preferable that the rotation direction of the rollers 34 be opposite to the travelling direction of the head units 31 and 32.

In the curing step, the engine of the three-dimensional object producing apparatus 30 causes the carriage 35 to move the ultraviolet irradiators 33, to irradiate the liquid film formed in the discharging step with ultraviolet rays corresponding to the wavelength of the photopolymerization initiator contained in the model part forming material and the support part forming material. Through this operation, the three-dimensional object producing apparatus 30 cures the liquid film and forms a layer.

After the bottommost layer is formed, the engine of the three-dimensional object producing apparatus 30 moves the stage down by a distance corresponding to the thickness of one layer.

The engine of the three-dimensional object producing apparatus 30 causes liquid droplets of the model part forming material 1 and liquid droplets of the support part forming material 2 to be discharged based on two-dimensional image data representing the second cross-section from the bottom while moving the carriage 35 or the stage 37. The discharging method is the same as when the bottommost liquid film is formed. As a result, a liquid film having the cross-sectional shape represented by the second two-dimensional data from the bottom is formed on the bottommost layer. Then, the engine of the three-dimensional object producing apparatus 30 causes the carriage 35 to move the ultraviolet irradiators 33 to irradiate the liquid film with ultraviolet rays, to cure the liquid film and form the second layer from the bottom on the bottommost layer.

The engine of the three-dimensional object producing apparatus 30 repeats forming and curing of a liquid film in the same manner as described above using the input two-dimensional data in the order of data closer to the bottom, to laminate layers. The number of times to repeat varies depending on the number of the input two-dimensional image data or, for example, the height and shape of the three-dimensional model. When object production using all of the two-dimensional image data is completed, a model part object in a state of being supported by a support part is obtained.

The object produced by the three-dimensional object producing apparatus 30 includes the model part and the support part. The support part is removed from the object after object production. The removing method is classified into physical removal and chemical removal. In the physical removal, a mechanical force is applied to remove the support part. On the other hand, in the chemical removal, the support part is disintegrated and removed by immersion in a solvent. The method for removing the support part is not particularly limited, but the chemical removal is more preferable because the object may be broken by the physical removal. Moreover, when costs are taken into consideration, a removing method by immersion in water is more preferable. When the removing method by immersion in water is employed, a support part forming material, of which a cured product has water disintegrability, is selected.

A three-dimensional object produced by the three-dimensional object producing method of the present disclosure and the three-dimensional object producing apparatus of the present disclosure has biocompatibility, and has a high elastic modulus, a high strength, and a high hardness at the same time as described below. Hence, the three-dimensional object can be suitably used as, for example, dental materials such as an artificial tooth.

In the present specification, an "artificial tooth" represents a tooth that is formed artificially to be used in order to restore the function of a natural tooth that is lost due to, for example, dental caries, trauma, and gum disease, and a laminate that is attached to the surface of a natural tooth in order to improve aesthetics.

Examples of a part of the tooth include an inlay, an onlay, a crown, and a bridge.

Examples of the whole of the tooth include an implant, and a denture such as a false tooth.

The three-dimensional object can be suitably used as, for example, eyeglass frames, shoe outsoles and middle soles, grips such as wheel grips, hearing aids, earphones, denture bases, and prosthetic limbs in addition to dental materials such as an artificial tooth.

The Vickers hardness of the three-dimensional object is preferably 22 or higher, more preferably 26 or higher, and yet more preferably 30 or higher.

For example, the Vickers hardness can be measured according to the procedure stipulated by JIS 22244.

The bending strength of the three-dimensional object is preferably 100 MPa or higher, more preferably 130 MPa or higher, and yet more preferably 160 MPa or higher.

To measure the bending strength, a universal tester (AUTOGRAPH, model No. AG-I, available from Shimadzu Corporation), a load cell for 1 kN, and a three-point bending jig are used. Stress that occurs when the distance between the fulcrums is 24 mm and the load point is displaced at a speed of 1 mm/minute is plotted with respect to the amount of strain, and the stress at the breaking point is determined as the maximum stress.

EXAMPLES

The present disclosure will be described below by way of Examples. The present disclosure should not be construed as being limited to these Examples.

Example 1

<Production of Curable Composition>

1,6-Bis(methacryloyloxy-2-ethoxycarbonylamino)-2,4,4-trimethylhexane (urethane dimethacrylate) (obtained from Sigma-Aldrich Co. LLC) serving as (Component 1) (42.0 parts by mass), diethylene glycol dimethacrylate (product name: NK ESTER 2G, obtained from Shin-Nakamura Chemical Co. Ltd.) serving as (Component 2) (28.0 parts by mass), and silica particles (product name: ADMANANO Y100SM-C6, having a volume mean primary particle diameter of 100 nm and a particle surface carbon content of 0.7% by mass, obtained from Admatechs Co., Ltd.) serving as (Component 3) (30.0% by mass) were mixed.

Next, diphenyl (2,4,6-trimethylbenzoyl) phosphine oxide (product name: OMNIRAD TPO H, obtained from BASF GmbH) serving as a photopolymerization initiator (3.0 parts by mass) was added and mixed with the resulting product.

Subsequently, the resulting product was filtrated through a filter (product name: CCP-FX-C1B, obtained from Advantech Co., Ltd., having an average pore diameter of 3 μm), to obtain a curable composition of Example 1.

Examples 2 to 9 and Comparative Examples 1 to 5

Curable compositions of Examples 2 to 9 and Comparative Examples 1 to 5 were obtained in the same manner as in Example 1, except that the composition and contents of Example 1 were changed to those presented in Table 1-1, Table 2-1, Table 3-1, Table 4-1 and Table 5-1.

Next, various properties of each obtained curable composition were evaluated in the manners described below. The results are presented in Table 1-2, Table 2-2, Table 3-2, Table 4-2, and Table 5-2.

<Method for Measuring Refractive Index>

—Method for Measuring Refractive Indices of Raw Materials (Before being Cured)—

The refractive indices of the raw materials (before being cured) were measured using an Abbe's refractometer NAR-1T (obtained from Atago Co., Ltd.) under D-rays (589.3 nm) of a light source lamp.

—Method for Measuring Refractive Index of Cured Product of Composition—

The refractive index of a cured product of each composition was measured using an Abbe's refractometer NAR-1T (obtained from Atago Co., Ltd.) under D-rays (589.3 nm) of a light source lamp.

—Method for Measuring Refractive Index of Component 3—

The refractive index of the component 3 was measured using the component 3 (commercial product) as is by the B method using an Abbe's refractometer and stipulated by JIS K 7142.

Specifically, an average refractive index of the component 3 calculated according to the following procedures of the B method using an Abbe's refractometer and stipulated by JIS K 7142 was used as the refractive index $n25D_{(3)}$ of the component 3, where the B method specifies that "When the sample is a powder, a pellet, or a granule, a sample quantity necessary for five or more times of measurement is prepared, and the refractive index is measured five times. Then, an average value having four significant digits is calculated".

<Method for Measuring Viscosity>

The viscosity of each curable composition was measured using a cone plate rotary viscometer (VISCOMETER TVE-22L obtained from TOKI SANGYO CO., LTD.) and evaluated according to the criteria described below. The temperature in the measuring vessel was fixed at 25° C. using a thermostatic circulation tank. As a rotor, a cone rotor (1° 34'×R24) was used. The grades A and B are levels sufficient for practical use.

[Evaluation Criteria]

A: The viscosity at 25° C. was 300 mPa·s or lower.

B: The viscosity at 25° C. was higher than 300 mPa·s and 400 mPa·s or lower.

C: The viscosity at 25° C. was higher than 400 mPa·s.

<Method for Measuring Total Light Transmittance Through Thickness of 1 mm>

<<Production of Test Piece for Transmittance Measurement>>

As illustrated in FIG. 2, an OHP sheet 41*a* was placed on a glass substrate 40*a*, and a silicon mold 42 (shape: a length of 20 mm on each side, and a thickness of 1 mm) was closely attached on the OHP sheet 41*a*. Next, the silicon mold 42 was filled with a curable composition 43, which was the measurement target, and covered with an OHP sheet 41*b*, which was further covered with a glass substrate 40*b*.

Next, using an ultraviolet irradiator (device name: SPOT CURE SP5-250DB obtained from Ushio Inc.), the curable composition was irradiated with ultraviolet rays having an irradiation intensity of 200 $mW/cm^2$ for 10 minutes through the glass substrate 40*b*. Next, using the ultraviolet irradiator, the curable composition was irradiated with ultraviolet rays having an irradiation intensity of 200 $mW/cm^2$ for 10 minutes through the glass substrate 40*a* at the side that was opposite to the side irradiated with ultraviolet rays first. Next, the OHP sheet 41*b* was peeled, and a cured product obtained through curing of the curable composition was taken out from the silicon mold 42 and left in a stationary state in an environment at a temperature of 23° C. at a relative humidity of 50% for 24 hours, to obtain a test piece having a thickness of 1 mm.

<<Method for Measuring Transmittance>>

The total light transmittance (Tt) through the test piece produced above in the thickness direction was measured using DIRECT READING HAZEMETER (obtained from Toyo Seiki Seisaku-sho, Ltd.) according to JIS K 7361-1/HAZE: JIS K 7136, and evaluated according to the evaluation criteria described below.

The grades A and B are levels sufficient for practical use.

[Evaluation Criteria]

A: The total light transmittance was 70% or higher.

B: The total light transmittance was 60% or higher and lower than 70%.

C: The total light transmittance was lower than 60%.

<Vickers Hardness (HV 0.2)>

A test piece for Vickers hardness measurement was produced in the same manner as in the production of the test piece for transmittance measurement, except that the size was changed to 40 mm in length, 10 mm in width, and 1 mm in average thickness.

The Vickers hardness of each obtained three-dimensional object was measured according to the procedure stipulated by JIS 22244, and evaluated according to the criteria described below. The grades A, B, and C are levels sufficient for practical use.

[Evaluation Criteria]

A: The Vickers hardness was 30 or higher.

B: The Vickers hardness was 26 or higher and lower than 30.

C: The Vickers hardness was 22 or higher and lower than 26.

D: The Vickers hardness was lower than 22.

<Method for Measuring Bending Strength>

A test piece for bending strength measurement was produced in the same manner as in the production of the test piece for transmittance measurement, except that the size was changed to 40 mm in length, 10 mm in width, and 1 mm in average thickness.

The bending strength of each obtained three-dimensional object was measured in the manner described below, and evaluated according to the criteria described below. For measuring the bending strength of each three-dimensional object, a universal tester (AUTOGRAPH, model No. AG-I, obtained from Shimadzu Corporation), a load cell for 1 kN, and a three-point bending jig were used. Stress that would occur when the distance between the fulcrums was 24 mm and the load point was displaced at a speed of 1 mm/minute was plotted with respect to the amount of strain, and the stress at the breaking point was determined as the maximum stress. The grades A to C are levels sufficient for practical use.

[Evaluation Criteria]

A: The bending strength was 160 MPa or higher.

B: The bending strength was 130 MPa or higher and lower than 160 MPa.

C: The bending strength was 100 MPa or higher and lower than 130 MPa.

D: The bending strength was lower than 100 MPa.

TABLE 1-1

| | | Material name | Raw material refractive index (n25D) | Viscosity (mPa · s), 25° C.) | Ex. 1 | Ex. 2 | Ex. 3 |
|---|---|---|---|---|---|---|---|
| Component 1 | (Meth) acrylate | 1,6-Bis (methacryloyloxy-2-ethoxycarbonylamino)-2,4,4-trimethylhexane (urethane dimethacrylate) | 1.49 | 8,000 | 42.0 | 28.0 | 42.0 |

TABLE 1-1-continued

| | | | Raw material refractive index | Viscosity (mPa · s), | Ex. | | |
|---|---|---|---|---|---|---|---|
| | | Material name | (n25D) | 25° C.) | 1 | 2 | 3 |
| Component 2 | (Meth) acrylate | LIGHT ESTER EG (monoethylene glycol dimethacrylate) | 1.45 | 3.0 | — | — | — |
| | | NK ESTER 2G (diethylene glycol dimethacrylate) | 1.46 | 5.0 | 28.0 | 30.0 | 14.0 |
| | | Methyl methacrylate | 1.41 | 0.5 | — | 12.0 | 14.0 |
| | Other (meth) acrylates | Bis-EMA (diethoxybisphenol A methacrylate) | 1.55 | 900 | — | — | — |
| | | LIGHT ESTER BZ (benzyl methacrylate) | 1.51 | 3.5 | — | — | — |
| Component 3 | Filler | ADMAFINE 3SM-C11 (volume mean primary particle dia.: 300 nm, silica, particle surface carbon content: 1.0% by mass) | 1.46 | — | — | — | 30.0 |
| | | ADMANANO Y100SM-C6 (volume mean primary particle dia.: 100 nm, silica, particle surface carbon content: 0.7% by mass) | 1.45 | — | 30.0 | 30.0 | — |
| | | ADMANANO Y100C-SM2 (volume mean primary particle dia.: 100 nm, silica, particle surface carbon content: 1.5% by mass) | 1.46 | — | — | — | — |
| | | ADMANANO YA10C-SM1 (volume mean primary particle dia.: 10 nm, silica, particle surface carbon content: 1.5% by mass) | 1.45 | — | — | — | — |
| | | ADMAFINE AO-502 (volume mean primary particle dia.: 300 nm, alumina | 1.46 | — | — | — | — |
| Polymerization initiator | | OMNIRAD TPO H (polymerization initiator) | — | — | 3.0 | 3.0 | 3.0 |
| | | Total (part by mass) | | | 103.0 | 103.0 | 103.0 |

TABLE 1-2

| | Ex. | | |
|---|---|---|---|
| | 1 | 2 | 3 |
| Content ratio of component 1 to component 2 (component 1:component 2) | 60:40 | 40:60 | 60:40 |
| Concentration (% by mass) of solid (component 3, filler) except initiator in composition | 30.0 | 30.0 | 30.0 |
| Refractive index (n20D) of cured product of composition | 1.51 | 1.50 | 1.52 |
| Difference between refractive index (n25D) of cured product of composition and refractive index (n25D)$_{(3)}$ of component 3 | 0.05 | 0.05 | 0.06 |
| Difference $\Delta n25D_{(1\_3)}$ between refractive index $n25D_{(1)}$ of component 1 and refractive index $n25D_{(3)}$ of component 3 | 0.04 | 0.04 | 0.03 |
| Difference $\Delta n25D_{(2\_3)}$ between refractive index $n25D_{(2)}$ of component | 0.00 | 0.00 | 0.01 |

TABLE 1-2-continued

| | | | Ex. | | |
|---|---|---|---|---|---|
| | | | 1 | 2 | 3 |
| 2 and refractive index $n25D_{(3)}$ of component 3 | | | | | |
| Evaluation result | Viscosity (mPa · s, 25° C.) | Measured value | 350 | 95 | 174 |
| | | Grade | B | A | A |
| | Vickers hardness (HV 0.2) | Measured value | 30 | 23 | 31 |
| | | Grade | A | C | A |
| | Bending strength (MPa) | Measured value | 185 | 110 | 162 |
| | | Grade | A | C | A |
| | Total light transmittance (Tt (%)) through thickness of 1 mm | Measured value | 71 | 74 | 62 |
| | | Grade | A | A | B |

TABLE 2-1

| | | Material name | Raw material refractive index (n25D) | Viscosity (mPa · s), 25° C. | Ex. 4 | Ex. 5 | Ex. 6 |
|---|---|---|---|---|---|---|---|
| Component 1 | (Meth) acrylate | 1,6-Bis (methacryloyloxy-2-ethoxycarbonylamino)-2,4,4-trimethylhexane (urethane dimethacrylate) | 1.49 | 8,000 | 36.0 | 48.0 | 48.0 |
| Component 2 | (Meth) acrylate | LIGHT ESTER EG (monoethylene glycol dimethacrylate) | 1.45 | 3.0 | — | — | — |
| | | NK ESTER 2G (diethylene glycol dimethacrylate) | 1.46 | 5.0 | 12.0 | 16.0 | 32.0 |
| | | Methyl methacrylate | 1.41 | 0.5 | 12.0 | 16.0 | — |
| | Other (meth) acrylates | Bis-EMA (diethoxybisphenol A methacrylate) | 1.55 | 900 | — | — | — |
| | | LIGHT ESTER BZ (benzyl methacrylate) | 1.51 | 3.5 | — | — | — |
| Component 3 | Filler | ADMAFINE 3SM-C11 (volume mean primary particle dia.: 300 nm, silica, particle surface carbon content: 1.0% by mass) | 1.46 | — | — | — | — |
| | | ADMANANO Y100SM-C6 (volume mean primary particle dia.: 100 nm, silica, particle surface carbon content: 0.7% by mass) | 1.45 | — | 40.0 | 20.0 | — |
| | | ADMANANO Y100C-SM2 (volume mean primary particle dia.: 100 nm, silica, particle surface carbon content: 1.5% by mass) | 1.46 | — | — | — | 20.0 |
| | | ADMANANO YA10C-SM1 (volume mean primary particle dia.: 10 nm, silica, particle surface carbon content: 1.5% by mass) | 1.45 | — | — | — | — |
| | | ADMAFINE AO-502 (volume mean primary particle dia.: 300 nm, alumina | 1.46 | — | — | — | — |
| Polymerization initiator | | OMNIRAD TPO H (polymerization initiator) | — | — | 3.0 | 3.0 | 3.0 |
| Total (part by mass) | | | | | 103.0 | 103.0 | 103.0 |

TABLE 2-2

| | Ex. 4 | Ex. 5 | Ex. 6 |
|---|---|---|---|
| Content ratio of component 1 to component 2 (component 1:component 2) | 60:40 | 60:40 | 60:40 |
| Concentration (% by mass) of solid (component 3, filler) except initiator in composition | 40.0 | 20.0 | 20.0 |
| Refractive index (n20D) of cured product of composition | 1.51 | 1.50 | 1.49 |
| Difference between refractive index (n25D) of cured product of composition and refractive index $(n25D)_{(3)}$ of component 3 | 0.06 | 0.05 | 0.03 |

TABLE 2-2-continued

| | | | Ex. 4 | Ex. 5 | Ex. 6 |
|---|---|---|---|---|---|
| Difference $\Delta n25D_{(1\_3)}$ between refractive index $n25D_{(1)}$ of component 1 and refractive index $n25D_{(3)}$ of component 3 | | | 0.04 | 0.04 | 0.03 |
| Difference $\Delta n25D_{(2\_3)}$ between refractive index $n250_{(2)}$ of component 2 and refractive index $n25D_{(3)}$ of component 3 | | | 0.01 | 0.01 | 0.00 |
| Evaluation result | Viscosity (mPa · s, 25° C.) | Measured value | 171 | 78 | 280 |
| | | Grade | A | A | A |

TABLE 2-2-continued

| | | Ex. 4 | Ex. 5 | Ex. 6 |
|---|---|---|---|---|
| Vickers hardness (HV 0.2) | Measured value | 36 | 27 | 29 |
| | Grade | A | B | B |
| Bending strength (MPa) | Measured value | 165 | 149 | 170 |
| | Grade | A | B | A |
| Total light transmittance (Tt (%)) through thickness of 1 mm | Measured value | 69 | 75 | 72 |
| | Grade | B | A | A |

TABLE 3-1

| | | Material name | Raw material refractive index (n25D) | Viscosity (mPa · s), 25° C.) | Ex. 7 | Ex. 8 | Ex. 9 |
|---|---|---|---|---|---|---|---|
| Component 1 | (Meth) acrylate | 1,6-Bis (methacryloyloxy-2-ethoxycarbonylamino)-2,4,4-trimethylhexane (urethane dimethacrylate) | 1.49 | 8,000 | 54.0 | 54.0 | 42.0 |
| Component 2 | (Meth) acrylate | LIGHT ESTER EG (monoethylene glycol dimethacrylate) | 1.45 | 3.0 | — | — | 28.0 |
| | | NK ESTER 2G (diethylene glycol dimethacrylate) | 1.46 | 5.0 | 36.0 | 36.0 | — |
| | | Methyl methacrylate | 1.41 | 0.5 | — | — | — |
| | Other (meth) acrylates | Bis-EMA (diethoxybisphenol A methacrylate) | 1.55 | 900 | — | — | — |
| | | LIGHT ESTER BZ (benzyl methacrylate) | 1.51 | 3.5 | — | — | — |
| Component 3 | Filler | ADMAFINE 3SM-C11 (volume mean primary particle dia.: 300 nm, silica, particle surface carbon content: 1.0% by mass) | 1.46 | — | — | — | — |
| | | ADMANANO Y100SM-C6 (volume mean primary particle dia.: 100 nm, silica, particle surface carbon content: 0.7% by mass) | 1.45 | — | — | — | 30.0 |
| | | ADMANANO Y100C-SM2 (volume mean primary particle dia.: 100 nm, silica, particle surface carbon content: 1.5% by mass) | 1.46 | — | — | — | — |
| | | ADMANANO YA10C-SM1 (volume mean primary particle dia.: 10 nm, silica, particle surface carbon content: 1.5% by mass) | 1.45 | — | 10.0 | — | — |
| | | ADMAFINE AO-502 (volume mean primary particle dia.: 300 nm, alumina | 1.46 | — | — | 10.0 | — |
| Polymerization initiator | | OMNIRAD TPO H (polymerization initiator) | — | — | 3.0 | 3.0 | 3.0 |
| | | Total (part by mass) | | | 103.0 | 103.0 | 103.0 |

TABLE 3-2

| | | | | | Ex. | |
|---|---|---|---|---|---|---|
| | | | | 7 | 8 | 9 |
| Content ratio of component 1 to component 2 (component 1:component 2) | | | | 60:40 | 60:40 | 60:40 |
| Concentration (% by mass) of solid (component 3, filler) except initiator in composition | | | | 10.0 | 10.0 | 30.0 |
| Refractive index (n20D) of cured product of composition | | | | 1.49 | 1.52 | 1.50 |
| Difference between refractive index (n25D) of cured product of composition and refractive index $(n25D)_{(3)}$ of component 3 | | | | 0.04 | 0.06 | 0.05 |
| Difference $\Delta n25D_{(1\_3)}$ between refractive index $n25D_{(1)}$ of component 1 and refractive index $n25D_{(3)}$ of component 3 | | | | 0.04 | 0.03 | 0.04 |
| Difference $\Delta n25D_{(2\_3)}$ between refractive index $n25D_{(2)}$ of component 2 and refractive index $n25D_{(3)}$ of component 3 | | | | 0.01 | 0.00 | 0.01 |
| Evaluation result | Viscosity (mPa · s, 25° C.) | Measured value | | 390 | 145 | 121 |
| | | Grade | | B | A | A |
| | Vickers hardness (HV 0.2) | Measured value | | 28 | 24 | 22 |
| | | Grade | | B | C | C |
| | Bending strength (MPa) | Measured value | | 110 | 109 | 114 |
| | | Grade | | C | C | C |
| | Total light transmittance (Tt (%)) through thickness of 1 mm | Measured value | | 76 | 60 | 70 |
| | | Grade | | A | B | A |

TABLE 4-1

| | | Material name | Raw material refractive index (n25D) | Viscosity (mPa · s), 25° C.) | Comp. Ex. 1 | Comp. Ex. 2 | Comp. Ex. 3 |
|---|---|---|---|---|---|---|---|
| Component 1 | (Meth) acrylate | 1,6-Bis (methacryloyloxy-2-ethoxycarbonylamino)-2,4,4-trimethylhexane (urethane dimethacrylate) | 1.49 | 8,000 | — | 60.0 | 49.0 |
| Component 2 | (Meth) acrylate | LIGHT ESTER EG (monoethylene glycol dimethacrylate) | 1.45 | 3.0 | — | — | — |
| | | NK ESTER 2G (diethylene glycol dimethacrylate) | 1.46 | 5.0 | 28.0 | 30.0 | 21.0 |
| | | Methyl methacrylate | 1.41 | 0.5 | — | 10.0 | — |
| | Other (meth) acrylates | Bis-EMA (diethoxybisphenol A methacrylate) | 1.55 | 900 | 42.0 | — | — |
| | | LIGHT ESTER BZ (benzyl methacrylate) | 1.51 | 3.5 | — | — | — |
| Component 3 | Filler | ADMAFINE 3SM-C11 (volume mean primary particle dia.: 300 nm, silica, particle surface carbon content: 1.0% by mass) | 1.46 | — | — | — | — |
| | | ADMANANO Y100SM-C6 (volume mean primary particle dia.: 100 nm, silica, particle surface carbon content: 0.7% by mass) | 1.45 | — | 30.0 | — | 30.0 |
| | | ADMANANO Y100C-SM2 (volume mean primary particle dia.: 100 nm, silica, particle surface carbon content: 1.5% by mass) | 1.46 | — | — | — | — |
| | | ADMANANO YA10C-SM1 (volume mean primary particle dia.: 10 nm, silica, particle surface carbon content: 1.5% by mass) | 1.45 | — | — | — | — |
| | | ADMAFINE AO-502 (volume mean primary particle dia.: 300 nm, alumina | 1.46 | — | — | — | — |

TABLE 4-1-continued

| | Material name | Raw material refractive index (n25D) | Viscosity (mPa · s), 25° C.) | Comp. Ex. 1 | 2 | 3 |
|---|---|---|---|---|---|---|
| Polymerization initiator | OMNIRAD TPO H (polymerization initiator) | — | — | 3.0 | 3.0 | 3.0 |
| | Total (part by mass) | | | 103.0 | 103.0 | 103.0 |

TABLE 4-2

| | Comp. Ex. 1 | 2 | 3 |
|---|---|---|---|
| Content ratio of component 1 to component 2 (component 1:component 2) | 0:100 | 60:40 | 70:30 |
| Concentration (% by mass) of solid (component 3, filler) except initiator in composition | 30.0 | 0.0 | 30.0 |
| Refractive index (n20D) of cured product of composition | 1.55 | 1.49 | — |
| Difference between refractive index (n25D) of cured product of composition and refractive index (n25D)$_{(3)}$ of component 3 | 0.10 | — | — |
| Difference $\Delta n25D_{(1\_3)}$ between refractive index n25D$_{(1)}$ of component 1 and refractive index n25D$_{(3)}$ of component 3 | 1.45 | 1.48 | 0.04 |
| Difference $\Delta n25D_{(2\_3)}$ between refractive index n250$_{(2)}$ of component | 0.01 | 1.45 | 0.01 |

TABLE 4-2-continued

| | | | Comp. Ex. 1 | 2 | 3 |
|---|---|---|---|---|---|
| 2 and refractive index n25D$_{(3)}$ of component 3 | | | | | |
| Evaluation result | Viscosity (mPa · s, 25° C.) | Measured value | 150 | 590 | 590 |
| | | Grade | A | C | C |
| | Vickers hardness (HV 0.2) | Measured value | 30 | 21 | Not inkjet dischargeable |
| | | Grade | A | D | |
| | Bending strength (MPa) | Measured value | 135 | 108 | |
| | | Grade | B | C | |
| | Total light transmittance (Tt (%)) through thickness of 1 mm | Measured value | 49 | 79 | |
| | | Grade | C | A | |

TABLE 5-1

| | | Material name | Raw material refractive index (n25D) | Viscosity (mPa · s), 25° C.) | Comp. Ex. 4 | 5 |
|---|---|---|---|---|---|---|
| Component 1 | (Meth) acrylate | 1,6-Bis (methacryloyloxy-2-ethoxycarbonylamino)-2,4,4-trimethylhexane (urethane dimethacrylate) | 1.49 | 8,000 | 42.0 | 21.0 |
| Component 2 | (Meth) acrylate | LIGHT ESTER EG (monoethylene glycol dimethacrylate) | 1.45 | 3.0 | — | — |
| | | NK ESTER 2G (diethylene glycol dimethacrylate) | 1.46 | 5.0 | — | 49.0 |
| | | Methyl methacrylate | 1.41 | 0.5 | — | — |
| | Other (meth) acrylates | Bis-EMA (diethoxybisphenol A methacrylate) | 1.55 | 900 | — | — |
| | | LIGHT ESTER BZ (benzyl methacrylate) | 1.51 | 3.5 | 28.0 | — |
| Component 3 | Filler | ADMAFINE 3SM-C11 (volume mean primary particle dia.: 300 nm, silica, particle surface carbon content: 1.0% by mass) | 1.46 | — | — | — |
| | | ADMANANO Y100SM-C6 (volume mean primary particle dia.: 100 nm, silica, particle surface carbon | 1.45 | — | 30.0 | 30.0 |

TABLE 5-1-continued

| | Material name | Raw material refractive index (n25D) | Viscosity (mPa · s), 25° C.) | Comp. Ex. 4 | Comp. Ex. 5 |
|---|---|---|---|---|---|
| | content: 0.7% by mass) | | | | |
| | ADMANANO Y100C-SM2 (volume mean primary particle dia.: 100 nm, silica, particle surface carbon content: 1.5% by mass) | 1.46 | — | — | — |
| | ADMANANO YA10C-SM1 (volume mean primary particle dia.: 10 nm, silica, particle surface carbon content: 1.5% by mass) | 1.45 | — | — | — |
| | ADMAFINE AO-502 (volume mean primary particle dia.: 300 nm, alumina | 1.46 | — | — | — |
| Polymerization initiator | OMNIRAD TPO H (polymerization initiator) | — | — | 3.0 | 3.0 |
| | Total (part by mass) | | | 103.0 | 103.0 |

TABLE 5-2

| | | | Comp. Ex. 4 | Comp. Ex. 5 |
|---|---|---|---|---|
| Content ratio of component 1 to component 2 (component 1:component 2) | | | 70:30 | 30:70 |
| Concentration (% by mass) of solid (component 3, filler) except initiator in composition | | | 30.0 | 20.0 |
| Refractive index (n20D) of cured product of composition | | | 1.53 | |
| Difference between refractive index (n25D) of cured product of composition and refractive index $(n25D)_{(3)}$ of component 3 | | | 0.08 | |
| Difference $\Delta n25D_{(1\_3)}$ between refractive index $n25D_{(1)}$ of component 1 and refractive index $n25D_{(3)}$ of component 3 | | | 0.04 | 0.04 |
| Difference $\Delta n25D_{(2\_3)}$ between refractive index $n25D_{(2)}$ of component 2 and refractive index $n25D_{(3)}$ of component 3 | | | 1.45 | 0.01 |
| Evaluation result | Viscosity (mPa · s, 25° C.) | Measured value | 340 | 103 |
| | | Grade | B | A |
| | Vickers hardness (HV 0.2) | Measured value | 8 | Not curable |
| | | Grade | D | |
| | Bending strength (MPa) | Measured value | 65 | |
| | | Grade | D | |
| | Total light transmittance (Tt (%)) through thickness of 1 mm | Measured value | 54 | |
| | | Grade | C | |

The particulars of each component presented in Table 1-1, Table 2-1, Table 3-1, Table 4-1, and Table 5-1 are as follows.

[Monomer Component]

—(Component 1) Multifunctional Urethane (Meth)Acrylate Monomer—

1,6-Bis(methacryloyloxy-2-ethoxycarbonylamino)-2,4,4-trimethylhexane (urethane dimethacrylate): obtained from Sigma-Aldrich Co. LLC, viscosity at 25° C.: 8,000 mPa·s, refractive index $n25D_{(1)}$ of raw material (before being cured): 1.485, refractive index n25D of cured product: 1.52

—(Component 2) (Meth)Acrylate Monomer—

NK ESTER 2G: Diethylene glycol dimethacrylate, obtained from Shin-Nakamura Chemical Co., Ltd., viscosity at 25° C.: 3.0 mPa·s, refractive index $n25D_{(2)}$ of raw material (before being cured): 1.458, refractive index n25D of cured product: 1.49

Methyl methacrylate: obtained from Mitsubishi Chemical Corporation, viscosity at 25° C.: 0.5 mPa·s, refractive index $n25D_{(2)}$ of raw material (before being cured): 1.414, refractive index n25D of cured product: 1.49

—Other (Meth)Acrylate Monomers—

Bis-EMA: Diethoxybisphenol A methacrylate, obtained from Sigma-Aldrich Co. LLC, viscosity at 25° C.: 900 mPa·s, refractive index $n25D_{(2)}$ of raw material (before being cured): 1.546, refractive index n25D of cured product: 1.58

LIGHT ESTER BZ: Benzyl methacrylate, obtained from Kyoeisha Chemical Co., Ltd., viscosity at 25° C.: 3.5 mPa·s, refractive index $n25D_{(2)}$ of raw material (before being cured): 1.512, refractive index n25D of cured product: 1.55

[Inorganic Filler]

ADMAFINE 3SM-C11: silica, volume mean primary particle diameter: 300 nm, obtained from Admatechs Co., Ltd., spherical shape, methacrylation by a silane coupling agent, particle surface carbon content: 1.0% by mass, refractive index $n25D_{(3)}$: 1.46

ADMANANO Y100SM-C6: silica, volume mean primary particle diameter: 100 nm, obtained from Admatechs Co., Ltd., spherical shape, methacrylation by a silane coupling agent, particle surface carbon content: 0.7% by mass, refractive index $n25D_{(3)}$: 1.45

ADMANANO Y100C-SM2: silica, volume mean primary particle diameter: 100 nm, obtained from Admatechs Co., Ltd., spherical shape, methacrylation by a silane coupling agent, particle surface carbon content: 1.5% by mass, refractive index $n25D_{(3)}$: 1.45

ADMANANO YA10C-SM1: silica, volume mean primary particle diameter: 10 nm, obtained from Admatechs Co., Ltd., spherical shape, methacrylation by a silane coupling agent, particle surface carbon content: 1.5% by mass, refractive index $n25D_{(3)}$: 1.45

ADMAFINE AO-502: alumina, volume mean primary particle diameter: 300 nm, obtained from Admatechs Co., Ltd., spherical shape, methacrylation by a silane coupling agent, particle surface carbon content: 0.7% by mass, refractive index $n25D_{(3)}$: 1.46

The volume mean primary particle diameter of the inorganic filler was a value measured by a dynamic light scattering method. The volume mean primary particle diameter of a product obtained by diluting a dispersion liquid of the inorganic filler 100-fold with 2-methoxy-1-methyl ethyl acetate was measured using a measuring instrument ELS-Z obtained from Otsuka Electronics Co., Ltd.

[Polymerization Initiator]

OMNIRAD TPO H: Diphenyl (2,4,6-trimethylbenzoyl) phosphine oxide, obtained from BASF GmbH "Difference in refractive indices" presented in Table 1-2, Table 2-2, Table 3-2, Table 4-2, and Table 5-2 represents an absolute value.

The results presented in Table 1-2, Table 2-2, Table 3-2, Table 4-2, and Table 5-2 revealed that the compositions of Examples 1 to 5 had a better inkjet dischargeability than that of the compositions of Comparative Examples 1 to 5 and could produce cured products (three-dimensional objects) having a higher strength and a higher transparency than those of cured products produced by the compositions of Comparative Examples 1 to 5.

The result of Example 1 in which the ratio "component 1:component 2" was 60:40 revealed that the composition was inkjet-dischargeable and could produce a cured product (three-dimensional object) having a high strength and a high transparency.

The result of Example 2 in which the ratio "component 1:component 2" was 40:60 revealed that the composition was curable although a cured product thus obtained had a lower Vickers hardness and a lower bending strength than those obtained in Example 1, and had a lower viscosity than that of the composition of Example 1.

The result of Example 3 in which the volume mean primary particle diameter of silica particles was changed to 300 nm from the value in Example 1 revealed that the composition likewise was inkjet-dischargeable and could produce a cured product (three-dimensional object) having a high strength and a high transparency.

The result of Example 5 revealed that the composition could produce a cured product (three-dimensional object) having a high hardness and a strength even though the content of (Component 3) inorganic filler was a low level of 20% by mass.

The result of Comparative Example 1 revealed that a cured product (three-dimensional object) obtained had a low total light transmittance Tt because Bis-EMA having a high refractive index as a raw material before being cured was used in the composition, and that the obtained curd product also had a poorer bending strength than that obtained in Example 1 in which urethane dimethacrylate was used as (Component 1).

The result of Comparative Example 3 in which the proportion of (Component 1) in all monomer components was 70% by mass or greater revealed that the composition was thickened and not inkjet-dischargeable.

The result of Comparative Example 4 in which (Component 2) was a monomer having a low viscosity and a high refractive index (1.512) revealed that not only was total light transmittance poor, but also strength was significantly poor.

The result of Comparative Example 5 revealed that the composition was not curable when the content of (Component 1) became approximately 30% by mass, which was the result of increasing the mass proportion of (Component 2) in all monomer components in order to reduce the viscosity of the composition, which presumably entailed a significant reduction in the mass proportion of (Component 1) in all monomer components.

Further, the present invention is not limited to these embodiments, but various variations and modifications may be made without departing from the scope of the present invention.

What is claimed is:

1. A curable composition, comprising:

a multifunctional urethane (meth)acrylate monomer, represented as component 1;

a (meth)acrylate monomer, represented as component 2; and an inorganic filler, represented as component 3, wherein a mass content ratio (component 1:component 2) of the component 1 to the component 2 is from 65:35 through 40:60.

2. The curable composition according to claim 1, wherein a refractive index difference $\Delta n25D_{(1\_3)}$ between a refractive index $n25D_{(1)}$ of the component 1 and a refractive index $n25D_{(3)}$ of the component 3 is 0.07 or less.

3. The curable composition according to claim 1, wherein a refractive index difference $\Delta n25D_{(2\_3)}$ between a refractive index $n25D_{(2)}$ of the component 2 and a refractive index $n25D_{(3)}$ of the component 3 is 0.07 or less, and a viscosity of the component 2 at 25° C. is 50 mPa·s or lower.

4. The curable composition according to claim 1, wherein a refractive index $n25D_{(3)}$ of the component 3 is 1.40 or higher and 1.50 or lower.

5. The curable composition according to claim 1, wherein a refractive index $n25D_{(2)}$ of the component 2 is 1.48 or lower.

6. The curable composition according to claim 1, wherein the component 2 includes either or both of ethylene glycol dimethacrylate (n=1) and diethylene glycol dimethacrylate (n=2), which are represented by General formula (2) below, General formula (2)

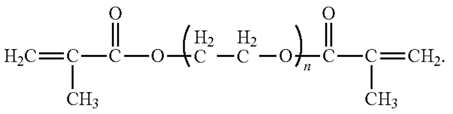

7. The curable composition according to claim 1, wherein the component 2 includes a monofunctional (meth)acrylate having a refractive index n25D of 1.48 or lower and a viscosity of 50 mPa·s or lower at 25° C.

8. The curable composition according to claim 1, wherein the component 1 is an aliphatic urethane dimethacrylate represented by Structural formula (1) below, and a refractive index $n25D_{(1)}$ of the aliphatic urethane dimethacrylate is 1.50 or lower, Structural formula (1)

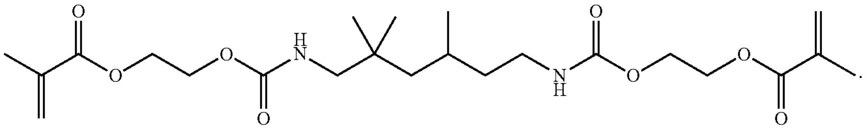

9. The curable composition according to claim 1, wherein a content of the component 3 is 20% by mass or greater and 60% by mass or less relative to a total amount of the component 1 and the component 2.

10. The curable composition according to claim 1, wherein a volume mean primary particle diameter of the component 3 is 10 nm or greater and 300 nm or less, and the component 3 includes silica particles.

11. The curable composition according to claim 10, wherein carbon is contained in surfaces of the silica particles, and a content of the carbon is 0.5% by mass or greater and 1.5% by mass or less relative to a mass of the silica particles.

12. The curable composition according to claim 1, wherein a viscosity of the curable composition at 25° C. is 400 mPa·s or lower.

13. A storage container, comprising the curable composition of claim 1, wherein the curable composition is stored in the storage container.

14. A three-dimensional object producing method, comprising:

discharging the curable composition of claim 1 by an inkjet method; and curing the curable composition by irradiation with active energy rays.

15. The curable composition according to claim 1, wherein the content of the component 1 is 40% by mass or greater relative to the whole amount of the curable composition.

16. The curable composition according to claim 15, wherein the content of the component 2 is 35% by mass or greater.

17. The curable composition according to claim 1, wherein the inorganic filler content in the composition is about 19% to about 39%.

18. The curable composition according to claim 12, wherein the inorganic filler content in the composition is about 19% to about 39%.

19. The curable composition according to claim 12, wherein the content of the component 1 is 40% by mass or greater and 65% by mass or less relative to the whole amount of the curable composition, wherein the content of the component 2 is 35% by mass or greater and 60% by mass or less relative to the whole amount of the curable composition, and wherein the content of the component 3 is 19% by mass or greater and 60% by mass or less relative to a total amount of the component 1 and the component 2.

20. The curable composition according to claim 12, wherein the content of the component 1 is 50% by mass or greater and 60% by mass or less relative to the whole amount of the curable composition, wherein the content of the component 2 is 40% by mass or greater and 50% by mass or less relative to the whole amount of the curable composition, and wherein the content of the component 3 is 19% by mass or greater and 40% by mass or less relative to a total amount of the component 1 and the component 2.

* * * * *